US00PP13601P2

(12) United States Plant Patent
Klemm

(10) Patent No.: US PP13,601 P2
(45) Date of Patent: Feb. 25, 2003

(54) POINSETTIA PLANT NAMED 'KLEPOPISA'

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/036,931

(22) Filed: Dec. 31, 2001

(51) Int. Cl.[7] ..... A01H 5/00

(52) U.S. Cl. ..... Plt./306

(58) Field of Search ..... Plt./306, 303

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Klepopisa', characterized by its uniform, upright and outwardly spreading plant habit; medium green-colored leaves with green-colored petioles; pink-colored flower bracts; early flowering habit; and good post-production longevity.

1 Drawing Sheet

BOTANICAL CLASSIFICATION/CULTIVAR DENOMINATION

*Euphorbia pulcherrima* Willd. cultivar Klepopisa.

BACKGROUND OF THE INVENTION

The present Invention relates to a new and distinct cultivar of Poinsettia plant, botanically known as *Euphorbia pulcherrima* Willd., and hereinafter referred to by the name 'Klepopisa'.

The new Poinsettia is a product of a mutation induction breeding program conducted by the Inventor in Stuttgart, Germany. The objective of the program is to create new Poinsettia cultivars with attractive flower bract coloration and uniform plant habit.

The new Poinsettia originated by exposing cuttings of the Poinsettia cultivar Kleposan, not patented, to X-ray radiation in Stuttgart, Germany. After the radiation treatment, cuttings were planted and flowered. The cultivar Klepopisa was discovered and selected by the Inventor as a single flowering plant in 1997. The selection of this plant was based on its attractive flower bract coloration and uniform plant habit.

Asexual reproduction of the new Poinsettia by vegetative terminal cuttings taken at Stuttgart, Germany since 1998, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Klepopisa'. These characteristics in combination distinguish 'Klepopisa' as a new and distinct Poinsettia cultivar:

1. Uniform, upright and outwardly spreading plant habit.
2. Medium green-colored leaves with green-colored petioles.
3. Pink-colored flower bracts.
4. Early flowering; response time, about 7.5 weeks.
5. Good post-production longevity.

Plants of the new Poinsettia differ primarily from plants of the parent, the cultivar Kleposan, in flower bract coloration as plants of the cultivar Kleposan have red-colored flower bracts.

Plants of the new Poinsettia differ primarily from plants of the cultivar KLEW01052, U.S. Plant Patent application filed concurrently, in flower bract coloration as plants of the cultivar KLEW01052 have pink and white bi-colored flower bracts.

Plants of the new Poinsettia can also be compared to plants of the cultivar 15-84, disclosed in U.S. Plant Pat. No. 7,310. In side-by-side comparisons conducted in Stuttgart, Germany, plants of the new Poinsettia differed from plants of the cultivar 15-84 in the following characteristics:

1. Plants of the new Poinsettia flowered about four days earlier than plants of the cultivar 15-84.
2. Flower bract coloration of plants of the new Poinsettia was more uniform than flower bract coloration of plants of the cultivar 15-84.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a single flowering plant of 'Klepopisa' grown in a container.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype.

The aforementioned photographs, following observations and measurements describe plants grown in Stuttgart, Germany under commercial practice in a glass-covered greenhouse with day temperatures ranging from 20 to 30° C. and night temperatures ranging from 16 to 20° C. Cuttings were harvested in August and planted into 12-cm containers when rooted and pinched once. Plants were flowered under natural season short day/long night conditions. Plants were about 15 weeks from unrooted cuttings when the photographs and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Klepopisa.

Parentage: Induced mutation of *Euphorbia pulcherrima* Willd. cultivar Kleposan, not patented.

Propagation:

*Type cutting.*—Vegetative terminal cuttings.

*Time to initiate roots.*—Summer: About 12 days at 22° C. Winter: About 15 days at 22° C.

*Time to produce a rooted cutting.*—Summer: About 20 days at 22° C. Winter: About 23 days at 22° C.

*Root description.*—Fibrous and freely-branching.

Plant description:

*Growth habit.*—Uniform, upright and outwardly spreading plant habit; inverted triangle; top of plant rounded; vigorous.

*Plant height.*—About 25 to 35 cm.

*Plant diameter or spread.*—About 35 to 45 cm.

*Lateral branch description.*—Quantity per plant: About five to seven lateral branches develop after pinching. Length: About 25 cm. Diameter: About 5 to 10 mm. Internode length: About 2 to 5 cm. Texture: Smooth, glabrous. Color: 144A to 143C.

*Foliage description.*—Arrangement: Alternate, single. Quantity of leaves per lateral branch: About 8 to 15. Length: About 4 to 12 cm. Width: About 2 to 7 cm. Shape: Mostly ovate with irregular lobing. Apex: Acute to acuminate. Base: Obtuse. Margin: Entire with irregular lobing. Venation pattern: Pinnate. Texture, upper and lower surfaces: Glabrous, smooth. Color: Young foliage, upper surface: 144B. Young foliage, lower surface: 143C. Fully expanded foliage, upper surface: 137A. Fully expanded foliage, lower surface: 137C. Venation, upper surface: 137A. Venation, lower surface: 138D. Petiole: Length: About 3 to 5 cm. Diameter: About 2.5 mm. Texture: Glabrous, smooth. Color, upper and lower surfaces: 144B.

Inflorescence description:

*Inflorescence type and habit.*—Inflorences are compound corymbs of cyathia with colored flower bracts subtending the cyathia. Inflorescences not persistent.

*Fragrance.*—None detected.

*Natural flowering season.*—Autumn/winter; flower initiation and development is induced under short day/long night conditions.

*Response time.*—Early, about 7.5 weeks.

*Post-production longevity.*—Plants of the new Poinsettia maintain good substance and bract color for about three to four weeks under interior conditions and about four to five weeks under greenhouse conditions.

*Quantity of inflorescences.*—One per lateral branch; about five to seven per plant.

*Inflorescence size.*—Diameter: About 15 to 20 cm. Height (depth): About 2 to 5 cm.

*Flower bracts.*—Quantity of fully developed flower bracts per inflorescence: About six to eight. Length: About 7 to 12 cm. Width: About 4 to 7 cm. Shape: Mostly ovate with occasional irregular lobing. Apex: Acute to acuminate. Base: Obtuse. Margin: Entire with occasional irregular lobing. Texture, upper and lower surfaces: Glabrous, smooth. Surface: Slightly rugose. Color: Developing and fully developed bracts, upper surface: 51B; fading to 62A with subsequent development. Developing and fully developed bracts, lower surface: 49B. Venation, upper and lower surfaces: Same as flower bracts. Bract petiole: Length: About 1 to 3 cm. Diameter: About 2 mm. Texture: Glabrous, smooth. Color: 144B.

*Cyathia.*—Quantity of cyathia per corymb: About four to eight. Diameter of cyathia cluster: About 1.5 to 3 cm. Length: About 4 to 7 mm. Diameter: About 3 to 5 mm. Shape: Ovoid. Color, immature and mature: 143C.

*Nectaries.*—Quantity of nectaries per cyathium: One or two. Diameter: About 2 to 3 mm. Color: 12A to 14B.

*Peduncle.*—Length: About 1 to 2 mm. Diameter: About 1 mm. Aspect: Erect. Strength: Moderately strong. Texture: Glabrous, smooth. Color: 144A to 144B.

*Reproductive organs.*—Stamens: Quantity of stamens per cyathium: About 5 to 10. Anther shape: Ovoid. Anther length: About 1 mm. Anther color: 9A to 12A. Amount of pollen: Abundant. Pollen color: 9A to 12A. Pistils: Quantity of pistils per cyathium: One. Pistil length: About 3 to 5 mm. Style length: About 2 to 3 mm. Stigma color: 185A.

Disease/pest resistance: Resistance to pathogens and pests common to Poinsettias has not been observed on plants grown under commercial conditions.

It is claimed:

1. A new and distinct cultivar of Poinsettia plant named 'Klepopisa', as illustrated and described.

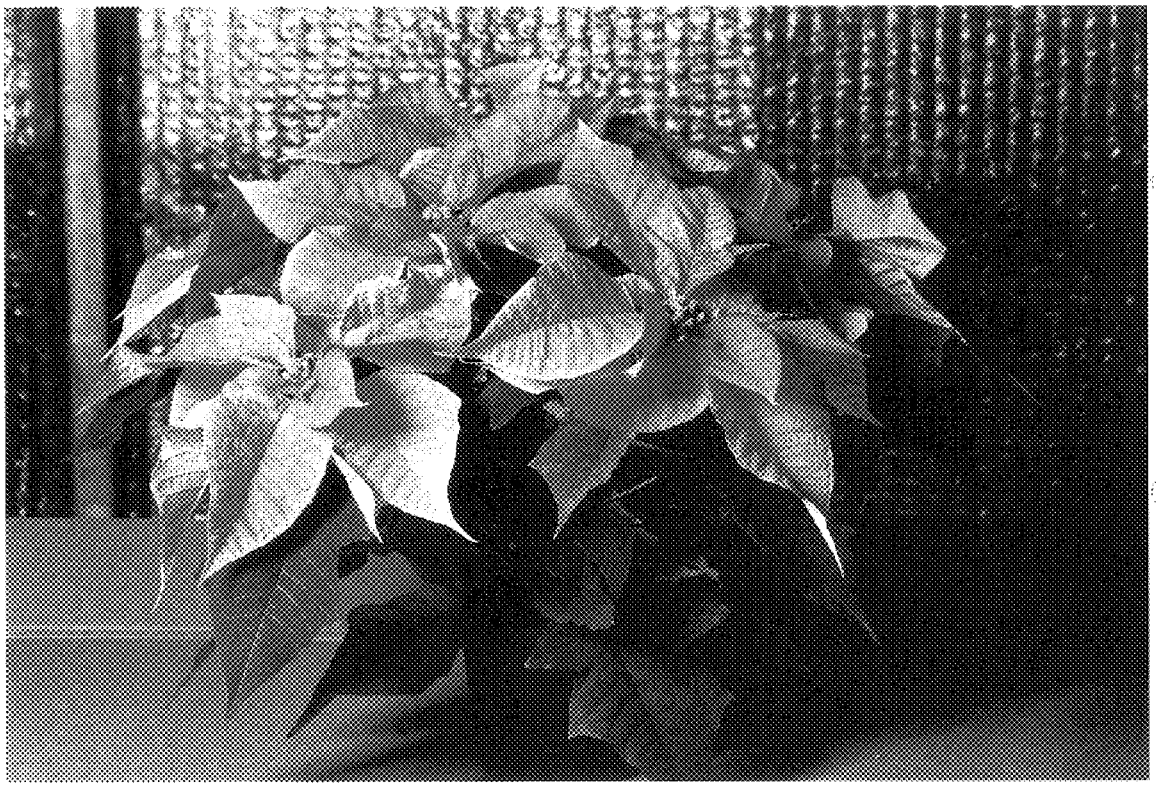

* * * * *